(12) United States Patent
Grosman et al.

(10) Patent No.: US 8,609,029 B2
(45) Date of Patent: Dec. 17, 2013

(54) ULTRASONIC SANITATION AND DISINFECTING DEVICE AND ASSOCIATED METHODS

(75) Inventors: Kurt E. Grosman, Orlando, FL (US); David W. Sparks, Thonotosassa, FL (US)

(73) Assignee: Zimek Technologies IP, LLC, Orlando, FL (US)

( * ) Notice: Subject to any disclaimer, the term of this patent is extended or adjusted under 35 U.S.C. 154(b) by 794 days.

(21) Appl. No.: 12/793,182

(22) Filed: Jun. 3, 2010
(Under 37 CFR 1.47)

(65) Prior Publication Data
US 2011/0030743 A1    Feb. 10, 2011

Related U.S. Application Data

(60) Division of application No. 12/047,732, filed on Mar. 13, 2008, now Pat. No. 7,780,909, and a continuation-in-part of application No. 11/624,317, filed on Jan. 18, 2007, now Pat. No. 7,959,859, and a continuation-in-part of application No. 11/277,176, filed on Mar. 22, 2006, now Pat. No. 8,062,588.

(51) Int. Cl.
*A61L 9/14* (2006.01)

(52) U.S. Cl.
USPC ............................ 422/128; 422/20; 239/102.2

(58) Field of Classification Search
USPC ................... 422/20, 128; 261/30; 239/102.2
See application file for complete search history.

(56) References Cited

U.S. PATENT DOCUMENTS

| | | | |
|---|---|---|---|
| 1,929,234 A | | 10/1933 | Anderson |
| 2,895,447 A | * | 7/1959 | Burrell ..................... 116/228 |
| 3,559,427 A | | 2/1971 | Baker |
| 3,561,444 A | | 2/1971 | Boucher |
| 3,729,138 A | | 4/1973 | Tysk |
| 3,828,773 A | | 8/1974 | Buch et al. |

(Continued)

FOREIGN PATENT DOCUMENTS

| | | |
|---|---|---|
| EP | 0571316 | 11/1993 |
| EP | 1288584 | 5/2003 |

(Continued)

OTHER PUBLICATIONS

English language machine translation of JP 08313019 A.*

(Continued)

*Primary Examiner* — Sean E Conley
(74) *Attorney, Agent, or Firm* — Allen, Dyer, Doppelt, Milbrath & Gilchrist, P.A.

(57) ABSTRACT

A device for sanitizing and disinfecting a space includes a tank having an interior space for holding an aqueous sanitizing, disinfecting, and/or sterilizing liquid, a bottom sector, an air inlet sector, and an exhaust sector, inner walls of the exhaust sector and the air inlet sector forming a substantially V-shaped air pathway within the interior space. A liquid cascading reactor vessel is positioned within the bottom sector of the tank, a top edge of the reactor vessel in adjustably spaced relation from a notch in the V-shaped air pathway. A vibratable ultrasonic head array is positionable within and beneath a top edge of the reactor vessel and is submergable within the reactor vessel for vibrating the disc to form atomized microparticles from the liquid. Air can be drawn into the air inlet, and the formed atomized micro-particles can be exhausted from the exhaust outlet.

21 Claims, 13 Drawing Sheets

(56) References Cited

U.S. PATENT DOCUMENTS

| | | | |
|---|---|---|---|
| 4,137,258 A | 1/1979 | Moore et al. |
| 4,366,125 A | 12/1982 | Kodera et al. |
| 4,385,911 A | 5/1983 | Popeil et al. |
| 4,410,139 A | 10/1983 | Nishikawa et al. |
| 4,517,159 A | 5/1985 | Karlson |
| 4,731,204 A | 3/1988 | Noma et al. |
| 5,017,199 A | 5/1991 | Etchepare |
| 5,300,260 A | 4/1994 | Keshet et al. |
| 5,611,967 A | 3/1997 | Jane et al. |
| 5,645,769 A | 7/1997 | Tamaru et al. |
| 5,653,919 A * | 8/1997 | White et al. ............... 261/21 |
| 5,783,117 A | 7/1998 | Byassee et al. |
| 5,868,999 A | 2/1999 | Karlson |
| 5,878,355 A | 3/1999 | Berg et al. |
| 6,102,992 A | 8/2000 | Berg et al. |
| 6,244,576 B1 | 6/2001 | Tsai |
| 6,245,361 B1 | 6/2001 | Merritt |
| 6,379,616 B1 | 4/2002 | Sherman |
| 6,379,633 B1 | 4/2002 | Garlick |
| 6,511,050 B2 * | 1/2003 | Chu ............................. 261/66 |
| 6,537,494 B2 | 3/2003 | Garlick |
| 6,589,481 B1 | 7/2003 | Lin et al. |
| 6,682,606 B2 | 1/2004 | Walker |
| 6,685,895 B1 | 2/2004 | Lin |
| 6,814,071 B2 | 11/2004 | Klimowicz et al. |
| 7,145,052 B1 | 12/2006 | Watkins |
| 7,524,454 B1 | 4/2009 | Sparks |
| 2003/0042629 A1 | 3/2003 | Eom |
| 2003/0127535 A1 | 7/2003 | Adiga et al. |
| 2003/0127753 A1 | 7/2003 | Bachert |
| 2003/0143110 A1 | 7/2003 | Kritzler et al. |
| 2004/0005240 A1 | 1/2004 | Adiga et al. |
| 2004/0009094 A1 | 1/2004 | Adiga et al. |
| 2004/0022673 A1 | 2/2004 | Protic |
| 2004/0057866 A1 | 3/2004 | Zumeris et al. |
| 2004/0146425 A1 | 7/2004 | Joshi |
| 2005/0031486 A1 | 2/2005 | Mole et al. |
| 2005/0074359 A1 | 4/2005 | Krieger et al. |
| 2005/0212152 A1 | 9/2005 | Reens |
| 2005/0214386 A1 | 9/2005 | Shaheen et al. |
| 2005/0220665 A1 | 10/2005 | Ding |
| 2006/0213508 A1 * | 9/2006 | Murray et al. ............ 128/200.16 |
| 2006/0216214 A1 | 9/2006 | Brown et al. |
| 2006/0249144 A1 * | 11/2006 | DeHaan et al. .......... 128/200.14 |
| 2006/0289490 A1 | 12/2006 | Mielnik |
| 2007/0193132 A1 | 8/2007 | Roscioli |
| 2008/0193650 A1 | 8/2008 | Lyon |

FOREIGN PATENT DOCUMENTS

| | | | |
|---|---|---|---|
| JP | 58-72000 | | 4/1983 |
| JP | 401116417 A | * | 5/1989 |
| JP | 8313019 | | 11/1996 |
| JP | 08313019 A | * | 11/1996 |
| JP | 11-123357 | | 5/1999 |
| JP | 2003-214664 | | 7/2003 |

OTHER PUBLICATIONS

English abstract for JP 401116417A; inventor: Maeda.*

* cited by examiner

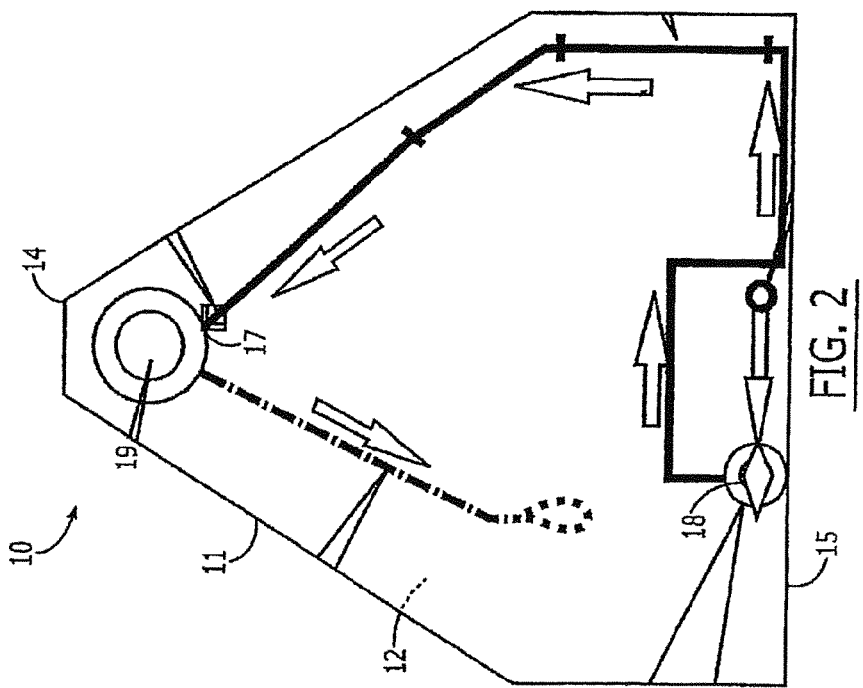
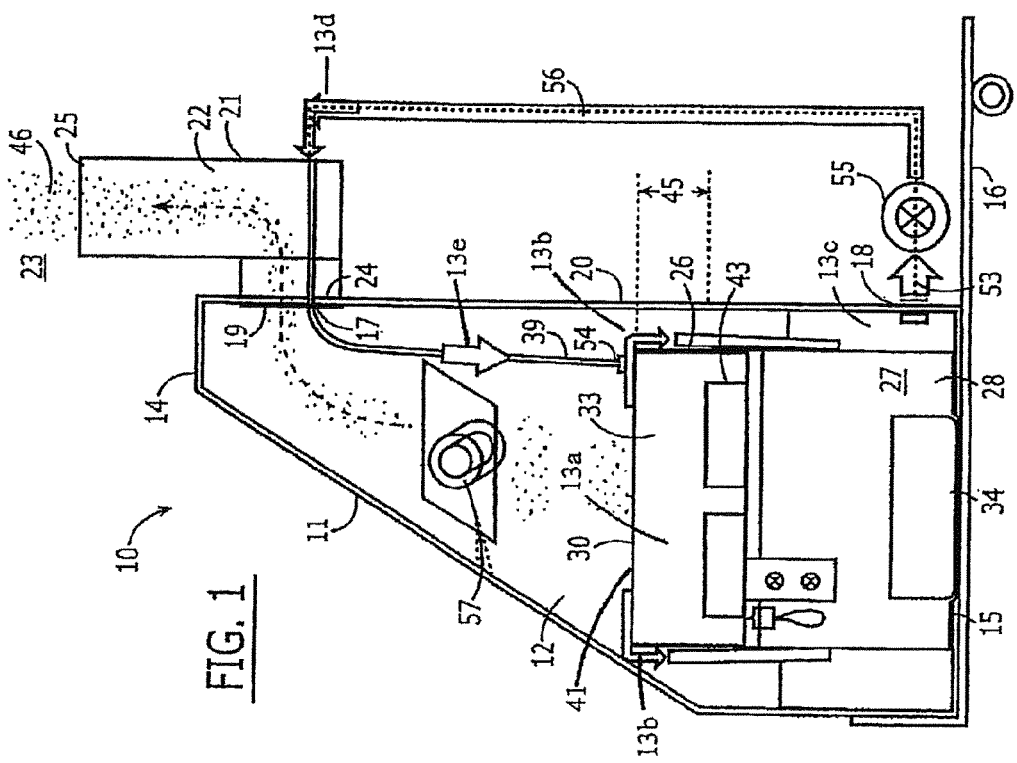

ULTRASONIC SANITATION AND DISINFECTING DEVICE AND ASSOCIATED METHODS

CROSS-REFERENCE TO RELATED APPLICATIONS

This application is a Divisional application of application Ser. No. 12/047,732 filed Mar. 13, 2008 for Ultrasonic Sanitation Device and Associated Methods which is a continuation-in-part of application Ser. No. 11/624,317 filed Jan. 18, 2007, which is itself a continuation-in-part of application Ser. No. 11/277,176 filed Mar. 22, 2006, the disclosures of which are herein incorporated by reference in their entirety, and all commonly owned.

FIELD OF THE INVENTION

The present invention relates to systems and methods for sanitizing and disinfecting enclosed spaces, and, more particularly, to such systems and methods that are capable of treating spaces three-dimensionally.

BACKGROUND

The sanitization and disinfection of enclosed spaces has become an issue of increasing importance owing to the possible presence of both natural and deliberately introduced contaminants. Since most commercial buildings are "sealed," that is, their windows cannot be opened, circulation of "fresh" air is typically not possible within a particular room. Similarly, most houses are now effectively sealed, with mostly processed air being circulated. In addition, some forms of conveyance, especially airplanes, are of necessity sealed against the environment during flight.

The enclosed nature of modern spaces has led to such problems as "sick building syndrome," since molds and mildews can flourish in enclosed, damp environments, and also to the possibility of the natural or deliberate introduction of more insidious threats to life, such as biological and chemical agents. Some infectious agents, such as hepatitis virus and staph bacteria such as MRSA, are known to survive in areas such as hospitals and other healthcare facilities, and there, as well as in other places such as cruise ships, schools, locker rooms, and correctional facilities, pose a health threat.

Another area of concern is the interior of vehicles, such as emergency vehicles. Such vehicles can include ambulances, fire rescue units, police cars, and other EMS vehicles. In addition, other publicly used vehicles such as buses, boats, subway cars, trains, and taxis can be of concern. These vehicles are seldom, if ever, cleaned to a level sufficient to ensure the eradication of infectious agents.

At present most sanitizing and disinfecting agents are "two-dimensional," that is, they are applied to accessible surfaces. For example, when disinfecting a table, typically the disinfectant is applied to the table top, but not the underside.

"Fogging" agents are known for eradicating pests such as fleas and other insects. Ionization-type purifiers are also known in the art that use electrostatic means to collect allergens and pollutants.

Therefore, it would be beneficial to provide a more effective device, system, and method for sanitizing and disinfecting enclosed spaces in a three-dimensional fashion.

SUMMARY OF THE INVENTION

The present invention provides a device for sanitizing and disinfecting a space. The device comprises a tank having an interior space for holding an aqueous sanitizing and disinfecting liquid, or, alternatively, a liquid sterilant. The words "sanitizing" and "disinfecting" are not intended as limitations, and one of skill in the art will recognize that the eradication of microbes can be referred to by a number of terms. A reactor vessel is supported within the interior space and above a bottom of the tank. Means are provided for maintaining a liquid depth in the tank interior space to a level beneath a top edge of the reactor vessel. An ultrasonic head array comprising an ultrasonically vibratable disc for generating ultrasonic energy is positionable within and beneath the top edge of the reactor vessel, which also acts as a cascade tray, wherein the liquid level is maintained substantially constant up to the top edge of the reactor vessel by causing spillage thereover. Means are included for transferring liquid from the tank interior space to the reactor vessel to a level for substantially submerging the ultrasonic head array, and, as the reactor vessel comprises a cascade tray, to, and over, the top edge in a preferred embodiment, the cascading liquid then returned to the tank interior space. Means are also provided for vibrating the disc to form an atomized fog of particles from the aqueous sanitizing liquid. Further means are provided for exhausting the formed atomized fog from the reactor vessel to a space exterior of the tank.

It is important to note that the term "atomized fog" is intended to mean herein a virtually dry "mist" comprising micro-particles having just enough moisture to allow for adhesion of the particles to a surface, such as within an interior space, but to leave substantially no apparent residue. Such a mist has been found to feel dry, and not wet. The dry "mist" fumigant created by the ultrasonic atomization process described herein does not constitute a gas, but rather a mass of micro-particles, each believed to comprise a completely formulated micro-particle of a disinfectant solution without substantial thermal or solubility degradation owing to heat or high-pressure particle generation.

The device may also be used to distribute a liquid by creating the atomized fog as above and directing the fog to a desired location, for example, for delivering fertilizer or pesticide to a plot of land, for watering plants, or for distributing a skin-care product to the skin of a user, although these uses are not intended to be limiting.

The device of the present invention is able to reach all areas in a space where air can penetrate, and, since the atomized particles have been found to remain airborne longer than conventional mists, treatment is more thorough, and less chemical is required to treat a surface area in a space than used by previously known atomization devices. A typical room of dimensions 12×12×10 ft can be disinfected and re-occupied in 20 min or less, for example.

An alternate embodiment of the device of the present invention is configured for use in sanitizing the interior of a vehicle. This embodiment includes a hose having a proximal end affixable in fluid communication with the exhaust outlet. Means for sealing an at least partially open access area of a vehicle is provided, wherein the sealing means has an aperture in fluid communication with a distal end of the hose. This embodiment of the invention is useful for enabling a sanitizing treatment of the vehicle's interior.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side cross-sectional view of an embodiment of the sanitizing device of the present invention.

FIG. 2 is a rear view of the device of FIG. 1.

DETAILED DESCRIPTION OF PREFERRED EMBODIMENTS

Figure 3:
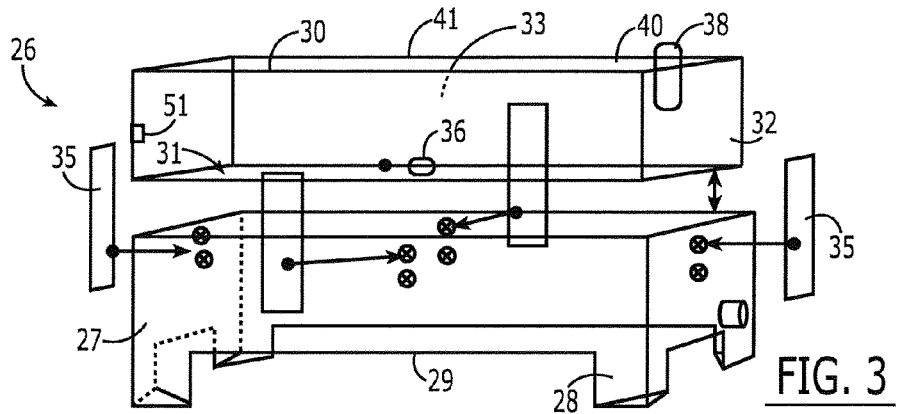
FIG. 3 is an exploded perspective view of the reactor vessel of the device of FIG. 1.
Figure 4:
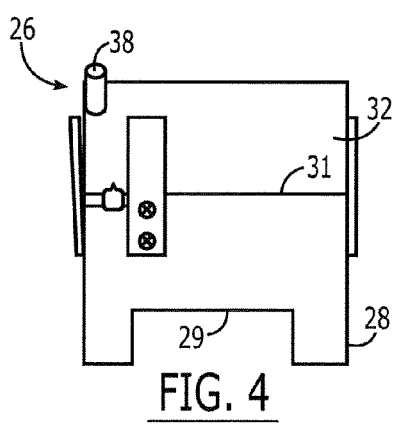
FIG. 4 is a side view of the reactor tray.
Figure 5:
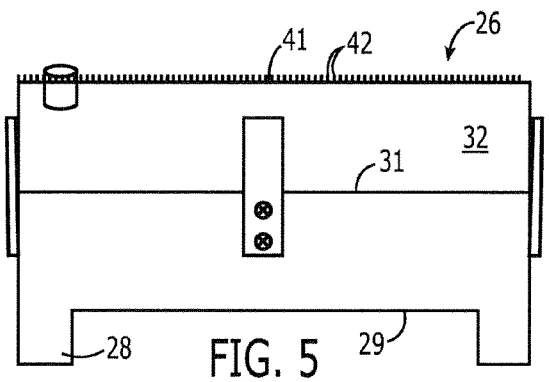
FIG. 5 is a rear view of the reactor tray.

A description of the preferred embodiments of the present invention will now be presented with reference to FIGS. 1-30.

The device 10 in a first embodiment for sanitizing and disinfecting a space includes a tank 11 (FIGS. 1 and 2) that has an interior space 12 for holding an aqueous sanitizing liquid 13. In a particular embodiment, the tank's top end 14 is substantially smaller than its bottom 15. Further, the tank 11 may be configured for placement upon a wheeled cart 16 for ease of transport.

The tank 11 has a liquid line aperture 17 adjacent the top 14 and a liquid outlet 18 adjacent the bottom 15. The tank 11 can comprise a material adapted to maintain a static charge, such as, but not intended to be limiting, a high-density polyethylene (HDPE) material.

A micro-particle outlet 19 is positioned adjacent the tank's top 14 along the rear wall 20, and is in fluid communication with a chimney 21 having a bore 22 therethrough leading to a space 23 exterior of the tank 11. In a preferred embodiment, the chimney bore 22 has an elbow therein, shown by the dotted line in FIG. 1, meeting the fog outlet 19 at a first end 24 and the exterior space 23 at the second, upwardly directed end 25.

A reactor vessel 26 is supported within the tank's interior space 12 and above the tank's bottom 15. In a particular embodiment illustrated in FIGS. 3-5, not intended to be limiting, the reactor vessel 26 comprises a substantially hollow rectangular lower section 27 that has a plurality of support legs 28 that extend from a bottom 29 thereof. An upper substantially rectangular section 30 comprises a bottom 31 and four enclosing walls 32 that extending upwardly from the upper section's bottom 31 and are adapted to contain liquid in the interior space 33 formed thereby. The lower 27 and the upper 30 sections are affixable together with the upper section 30 atop the lower section 27 and are positionable within the tank's interior space 12 with the support legs 28 contacting the bottom surface 34 of the tank's interior space 12. One of skill in the art will recognize that additional embodiments for the reactor tray 26 could be envisioned, and that the shape presented here in is intended to be exemplary only.

In a particular embodiment, not intended to be limiting, the reactor vessel 26 is formed in two parts 27, 30 in order to permit insertion into a particular tank 11. Here the parts 27, 30 are held together with the use of joiner clips 35 that are screwed onto the lower section 27 and serve to brace the sections 27,30 together. The reactor vessel 26 has one or more drain holes 36 or gravity-fed lines extending from the interior space 33 of the reactor vessel 26 to the tank's interior space 12 and is positioned adjacent the bottom 31 of the reactor vessel's interior space 33, or extends out of the reactor vessel's interior space by a hose to the tank's interior space 33.

The reactor vessel 26 further has affixed thereto a hose clamp 38 for supporting a liquid line 39, which will be discussed in the following. The top surface 40 of the upper section 30 should preferably have an area substantially greater than the top 14 of the tank 11.

Another feature of particular embodiments of the cascading reactor vessel 26 is that the top edge 41 of the upper section 30 can have a plurality of notches 42 therealong. These notches 42 can assist in permitting liquid to pass therethrough, but to substantially prevent foam from passing therethrough, thus retaining foam within the upper section 30 and not permitting it into the return line 39.

Figure 6:
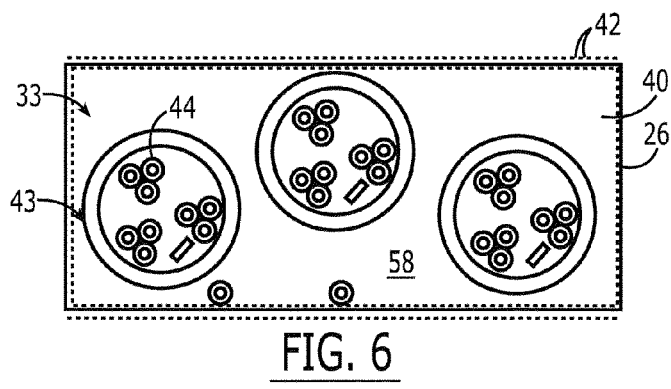
FIG. 6 is a top view of the reactor tray with ultrasonic head arrays positioned therein.
Figure 7:
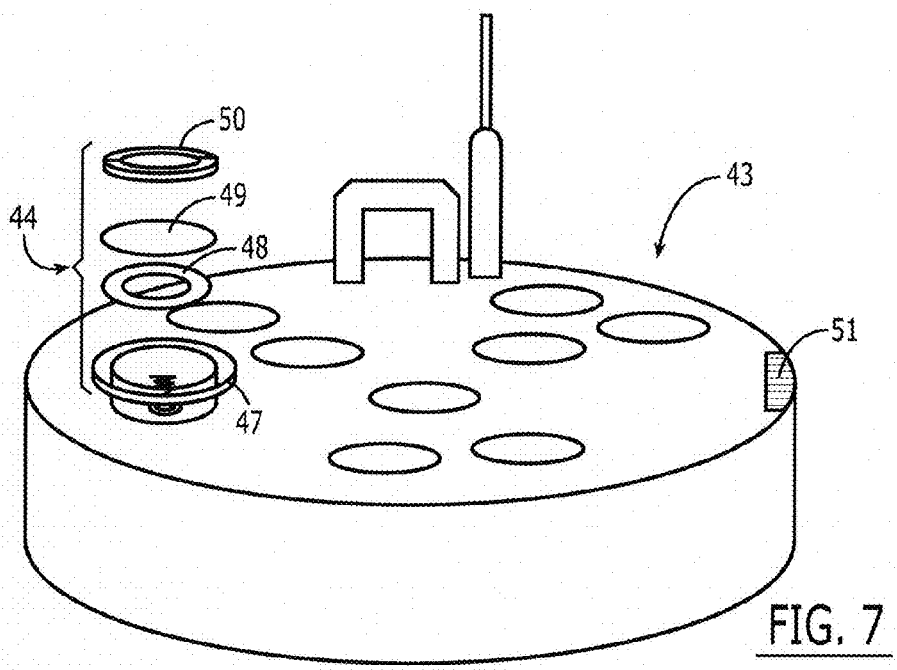
FIG. 7 is a side-top perspective view of an ultrasonic reactor head array, with one disk seen in exploded view.
Figure 8:
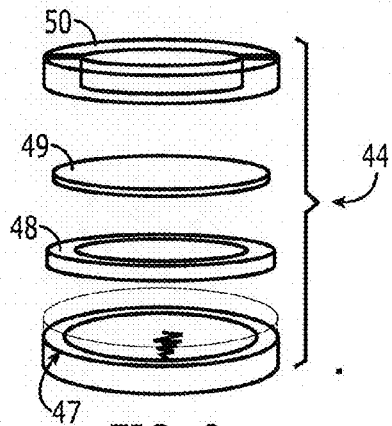
FIG. 8 is an exploded view of a reactor head array disk.

Positioned within the reactor vessel's upper section 30 is a plurality of ultrasonic head arrays 43, here, and three ultrasonic head arrays (FIGS. 6-8). Each of the head arrays 43 comprises a plurality, here, nine, vibratable heads 44 for generating ultrasonic energy, operating in a frequency range of 1.30-2.5 MHZ, with a preferred value of 1.70 MHZ. The head arrays 43 are positioned so as to be submersible within the reactor vessel 26, the submersion depth 45 optimized for production of an atomized fog 46 of particles from the liquid 13 therewithin. Preferably the fog 46 comprises negatively charged particles, which aid dispersal and space coverage. It has been found that the depth 45 of the liquid column and also the vibration frequency affects the focus of the sound waves.

The signal for activating the discs 44 is transmitted from devices known in the art, such as by way of a manual switch or level sensor.

The ultrasonic head arrays 43 can comprise head arrays such as can be obtained from Sonaer Ultrasonics (Farmingdale, N.Y.), although this is not intended as a limitation. An exemplary head array that can be used comprises part number T241, although this is not intended to be limiting. The fog 46 created by these head arrays 43 can contain particles in a range of 0.25-5.0 μm, although this is not intended to be limiting, as the size may be larger or smaller in some instances. Each of the discs 44 include a substantially toroidal O-ring seat 47, a Viton O-ring 48 seated on the O-ring seat 47, a ceramic disk 49 positioned atop the O-ring 48, and a substantially toroidal retaining ring 50 positioned in circumferentially retaining relation atop the ceramic disk 49. The discs 44 are known in the art to be supplied with silicone O-rings, but it has been found that the increased stiffness and chemical resistance of the Viton material is beneficial to the invention.

The drain hole 36 or drain hose discussed above has been found to be beneficial in extending the life of the device 10 by keeping the head arrays 43 dry. A level sensor 51 can also be provided for automatically turning the head arrays 43 on and off depending upon the presence or absence of liquid. The level sensor 51 can be positioned either on the tank 11 or on the head arrays 43 themselves.

Means are included for transferring liquid from the tank's interior space 12 to the reactor vessel 26 to a level for substantially submerging the ultrasonic head array 43. For this purpose is provided a liquid line 39 that is in fluid communication with the tank's liquid outlet 18 at an inlet end 53 and with the reactor vessel 26 at an outlet end 54. The liquid line 39 in this embodiment passes through the liquid line aperture 17 between the inlet end 53 and the outlet end 54, and is affixed to the reactor vessel 26 with the use of the hose clamp 38.

As illustrated with reference again to FIG. 1, a pump 55 is provided along the liquid line 39 that is operable to move liquid 13 through the liquid line 39 from the tank's interior space 12 beneath the reactor vessel 26, or above and then into the interior space 33 of the reactor vessel 26. The liquid 13 is pumped from the bottom 15 of the tank 11 through the liquid line 39 via the clear portion 56 and into the tank through the liquid line aperture 17 near the top end 14 of the tank. The liquid line outlet end 54 delivers the liquid into the upper section 30 of the reactor vessel 26 allowing the upper section 30 to be filled with liquid 13a and an overflow of liquid 13b (illustrated with arrows) to continuously cascade over the edge 41 into the bottom 15 of the tank 11 wherein the liquid 13c is pumped through the liquid outlet as the liquid 13d through the clear line portion 56 and to the liquid line aperture 17, and wherein the liquid 13e is delivered to the upper section 30 to repeat the cycle from liquid 13a. For one embodiment of the invention as herein described by way of example, the liquid line 39 comprise a substantially clear material, so that a portion 56 of the liquid line 39 exterior of the tank 11 can thereby serve as an indicator of a liquid level within the tank's interior space 12 when the pump 55 is not operating. Alternatively, another type of level sensor can be provided, as will be discussed in the following, and the liquid line 39 can comprise a non-transparent material. The placement of the liquid line portion 56 outside the tank 11 has also proven beneficial in assisting in cooling the liquid upon its pathway to the reactor vessel 26. In addition, a filtration element may be added to eliminate contaminants along the liquid line 39.

The device 10 further includes means for exhausting the atomized fog 46 that is formed to an exterior of the tank 11. This can be accomplished, for example, with the use of a fan 57 positioned within the tank's interior space 12 above the reactor vessel 26 and positioned to direct the formed atomized fog 46 from a top surface 58 of liquid 13 in the reactor vessel 26 to the fog outlet 19.

An additional feature that may be provided in certain circumstances includes a means for heating the fog 46, which has been found to reduce the size of the fog particles. Such a heating means may comprise, for example, a coil 59 (FIG. 10) positioned along the exhaust path.

Figure 9:
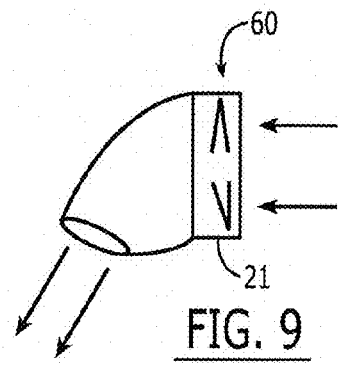
FIG. 9 is a side perspective view of an alternate embodiment of an exhaust system including a diverter element.
Figure 10:
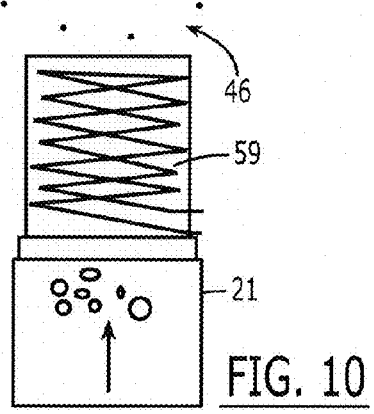
FIG. 10 is a side cross-sectional view of an alternate embodiment incorporating a heating exhaust.

It will be understood by one of skill in the art that many variations on the embodiment discussed above may be contemplated. For example, the exhaust system may include a diverter element 60 as illustrated in FIG. 9.

Figure 11A:
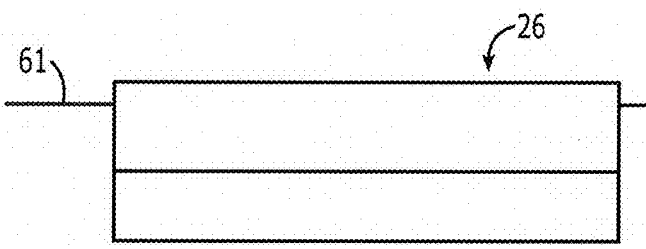
FIGS. 11A-11D are side cross-sectional views of different exemplary embodiments of the reactor tray.
Figure 11B:
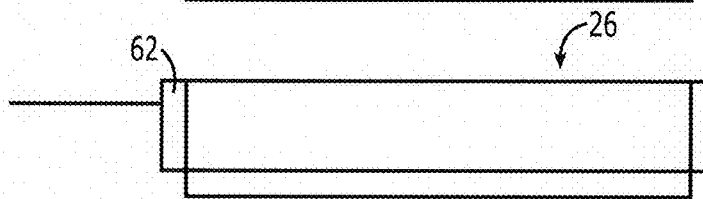
Figure 11C:
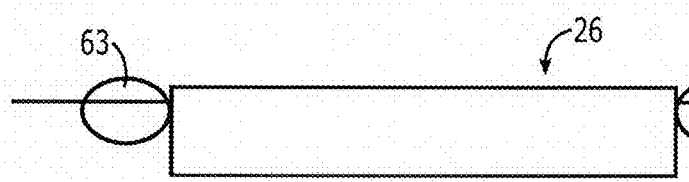
Figure 11D:
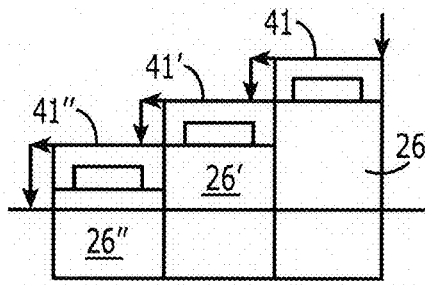
Figure 12:
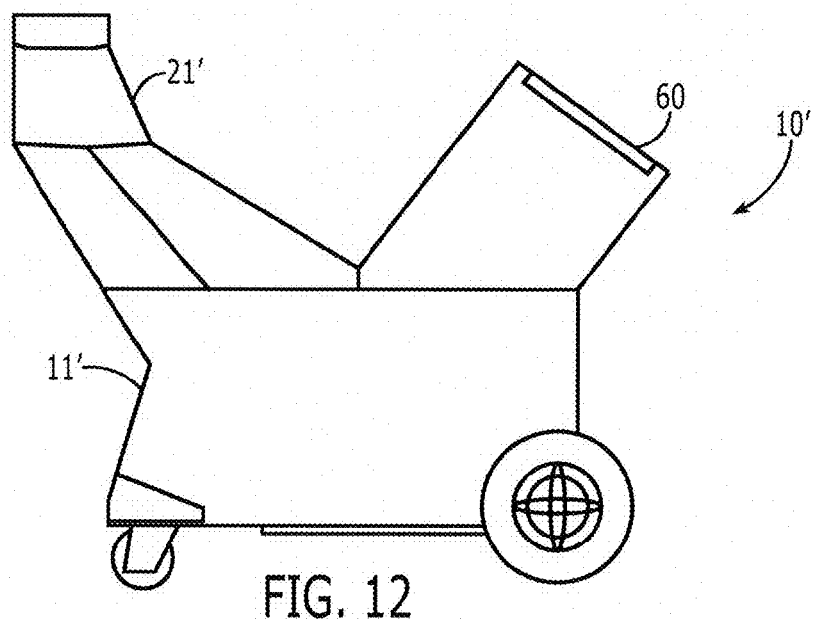
FIG. 12 is a schematic illustration of a side view of an alternate embodiment of the device.

In addition, various alternate means may be employed to support the ultrasonic head arrays 43, as shown in the flotation elements of FIGS. 11A-11C, wherein a foam floater 61 (FIG. 11A), a sealed air cavity 62 (FIG. 11B), or a floater ring 63 (FIG. 11C) may be used to support the tray 26 and the head arrays 43.

Further, the cascading reactor tray 26 may include a plurality of cascading reactor vessels 26, 26' 26" positioned adjacent each other, the top edge 41 of a first reactor vessel 26 above the top edge 41' of a second reactor vessel 26', and so on. In this embodiment the liquid transferring means is adapted to transfer liquid 13 into the first reactor vessel 26, thereby permitting a cascade of liquid from the first reactor vessel 26 into the second reactor vessel 26' and thence into the third reactor vessel 26" during operation.

The shape of the device as illustrated herein is not intended to be limiting. For example, in an alternate embodiment 10' shown in FIG. 12, the tank 11' may have a chimney 21' at the rear of the tank, which comprises a liquid inlet as well as an outlet for the dry mist created therein, and an air intake 60 toward the front of the tank 11'.

Figure 13:
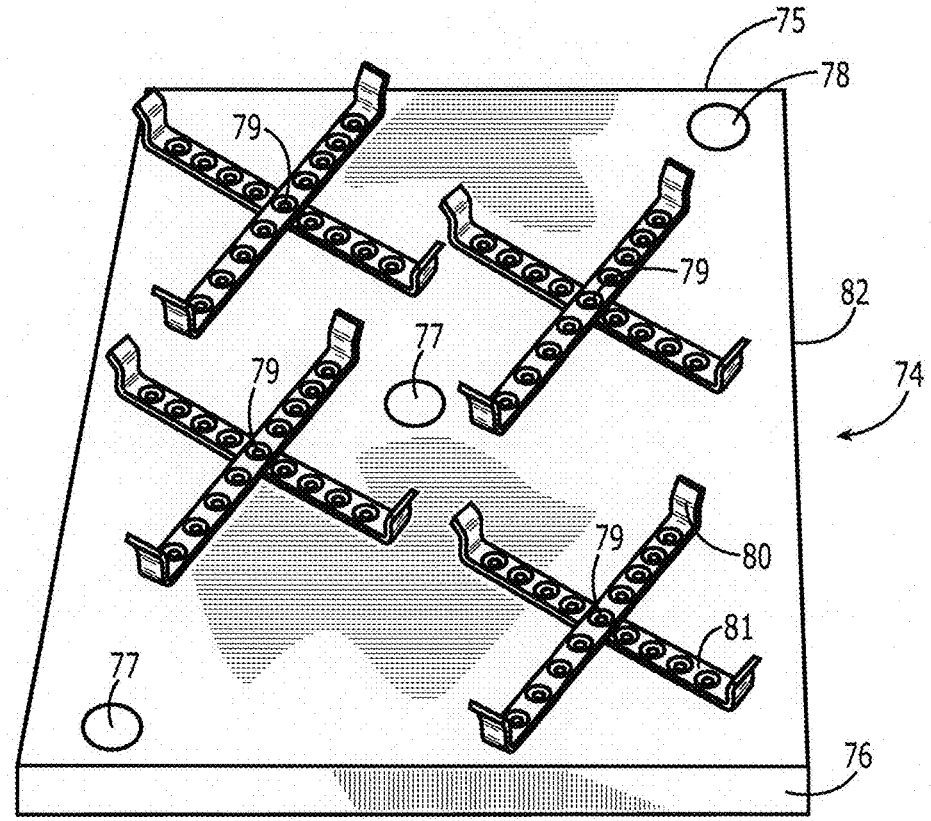
FIG. 13 is a top/side perspective view of the inside of a reactor vessel for the embodiment of FIG. 12.

Yet another embodiment 70 (FIGS. 13-24) comprises a reactor vessel having a smooth upper edge 75 on the lip 76, and two inlets 77 for filling the vessel 74 (FIG. 13). A drain 78 permits emptying the vessel 74.

The vessel 74 in this embodiment 70 is adapted to hold four ultrasonic head arrays 43 as described above within four reactor holders 79 positioned in spaced relation within the vessel 74. Each reactor holder 79 comprises an "X"-shaped element having upwardly extending clips 80 at the end of each arm 81, the clips 80 positioned to surround the periphery of each ultrasonic head array.

In this embodiment 70 the reaction holders 79 are affixed to the bottom 82 of the reactor vessel 74, for example, via glue such as epoxy, although this is not intended as a limitation. The holders 79 are beneficial in elevating the reactor head arrays so that treatment fluid may circulate under the reactor, helping to cool the head array. The holders 79 also permit a secure fit and easy removal of the head arrays for replacement or repair.

Figure 14:
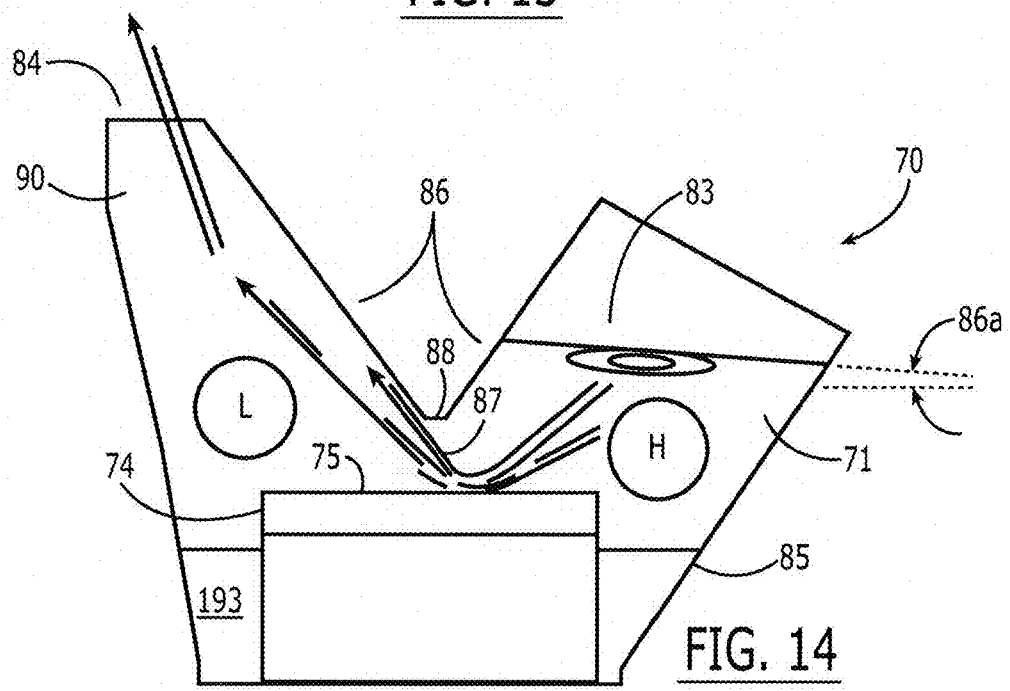
FIG. 14 is a side cross-sectional view of an inner tank.

The cross-sectional view of FIG. 14 illustrates airflow (shown as double arrows) for this embodiment 70. An inlet fan 83 at a front end of the tank 71 blows air toward the reactor vessel 74, and thence out the exhaust 84 at the rear end of the tank 71, carrying along with it the particles created by the ultrasonic head arrays. The fluid level 85 is shown surrounding the vessel 74.

In a particular embodiment, as illustrated with continued referenced to FIG. 14, the inlet fan 83 is mounted at an angle 86a of approximately 10 degrees to the horizontal. The shape of the tank 71 includes a substantially "V"-shaped compression region 86 leaving a gap 87 between the notch 88 of the "V"-shaped compression region 86 and the top 75 of the reactor vessel 74. As further illustrated, the air flow (double line arrows) is therefore moved from high pressure area, designated by circle H, to a low pressure area, designated by circle L. As is well known to those skilled in the art, and as described with Bernoulli's Principal, the speed of the air flow will increase as a result of the air flow moving from a relatively higher pressure area to a relatively lower pressure area. The higher speed of the air flow thus moves the smaller particles at a greater speed toward the exhaust 84, the larger and thus slower particles thus having a greater time to fall back toward the vessel 74 under an influence of gravity. The compression region 86 thus provides a culling out or filtering of smaller particles from the particles generated at the top 75 of the vessel 74. It will be understood by one of skill in the art that the compression region 86 can also be substantially "L"- or "J"-shaped, and can also be formed with the use of deflectors or baffles to create a desired compression region within or above the reaction zone above the vessel 74. Further, the compression region 86 can be adjusted according to the size of the tank, the area of the cascade tray, the type and size of the reactor heads, the orientation of the air flow, and the tilt of the air flow fan inlet. It will also be understood by one of skill in the art that the means of creating air flow over the fluid can be exterior to the unit 70 from an outside source.

Figure 15:
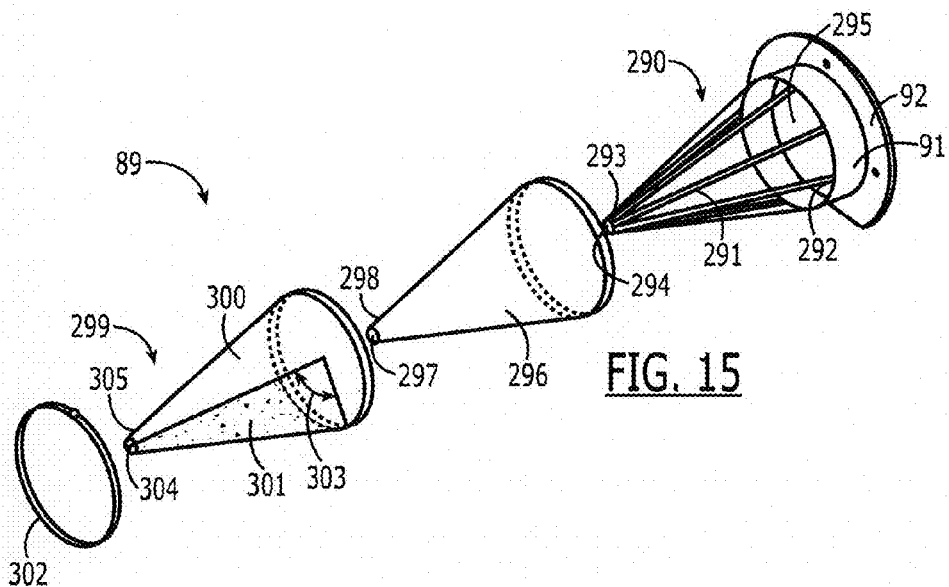
FIG. 15 is an exploded view of a particle filter.
Figure 16A:
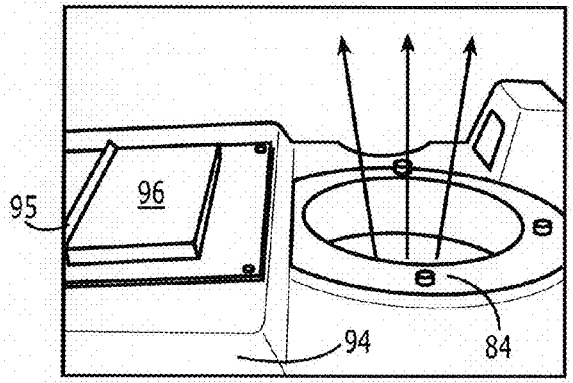
FIGS. 16A, 16B is a side perspective view of the mass blower operation.
Figure 16B:
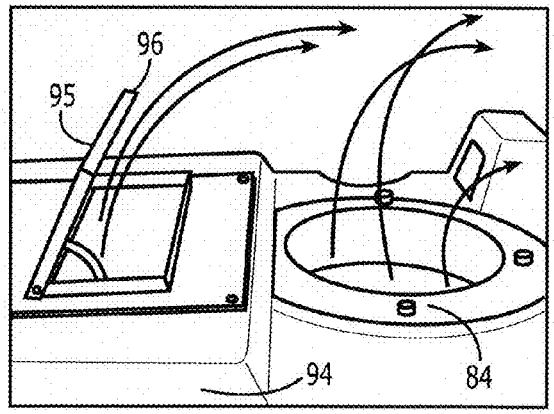
Figure 28:
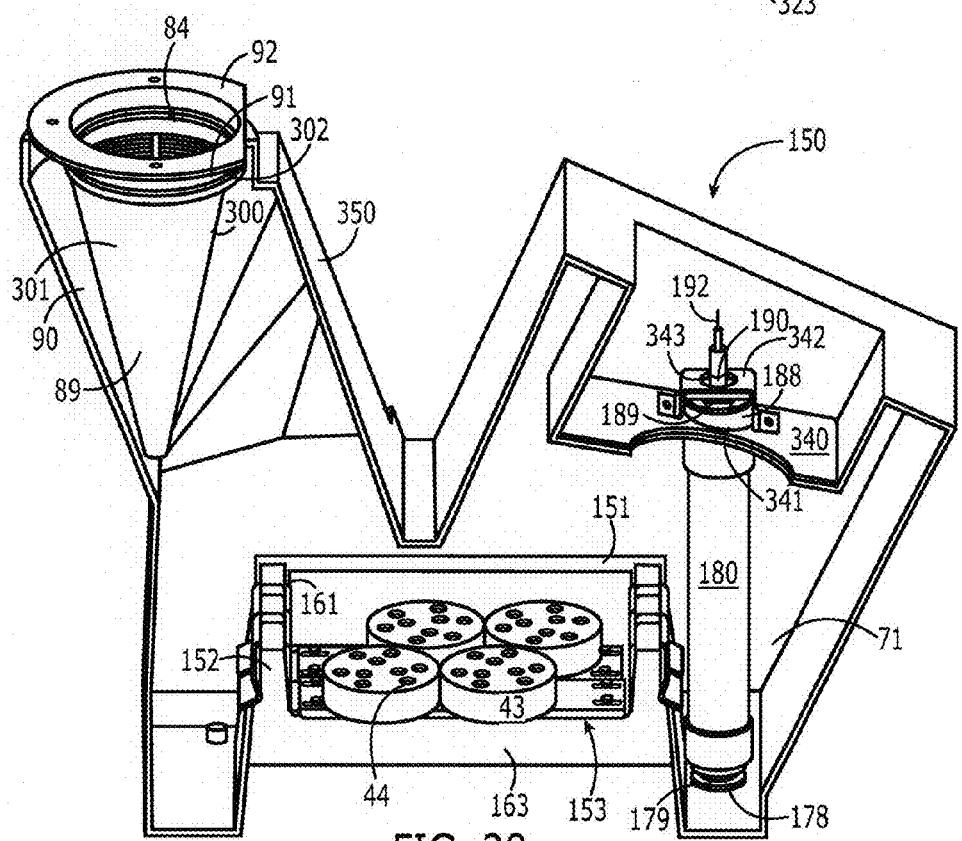
FIG. 28 is a side cutaway view of the device incorporating the reactor vessel bracket assembly of FIG. 27.
Figure 29:
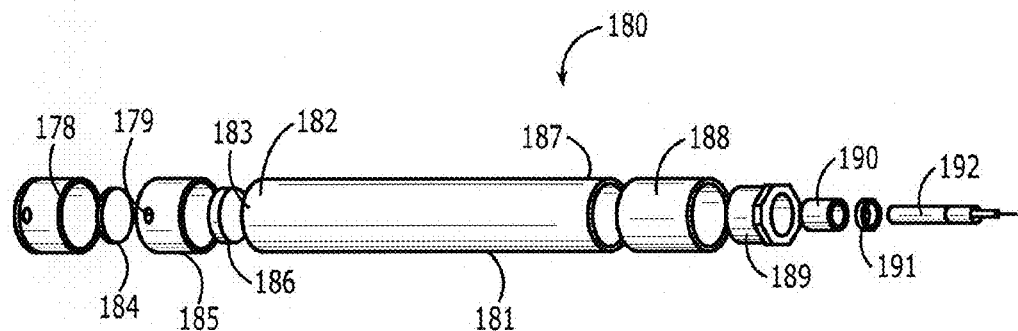
FIG. 29 is an exploded view of the level sensor.

This device 70 further comprises a particle filter 89 positioned within the chimney bore 90 (FIGS. 15 and 28). The particle filter 89 can comprise a substantially inverted cone-shaped element, although this is not intended as a limitation, and other shapes, such as "tear-drop" shape might also be contemplated. The particle filter 89 has a substantially cylindrical support base 91 having an upper toroidal lip 92 for supporting the filter 89 within the chimney bore 90 at the exhaust aperture 84. The filter 89 comprises a frame 290, which can comprise metal or plastic, although these are not intended as limitations. The frame 290 comprises a plurality of elongated ribs 291 affixed at top ends 292 to the filter base 91, and meeting at bottom ends 293 to define a small aperture 294, thereby forming a generally conical shape, with windows 295 defined by the ribs 291.

Positioned in surrounding relation to the frame 290 is a conical first filter element 296, comprising in a particular embodiment a ¼-in. plastic mesh, having an aperture 297 at a bottom end 298. Positioned in surrounding relation to the first filter element 296 is a conical second filter element 299, comprising in a particular embodiment a mesh comprising, for example, nylon or plastic, and having an aperture 304 at a bottom end 305. The mesh comprises a first mesh 300 comprising a 0.088-in. mesh and a second mesh 301 comprising a 0.05-in. mesh. The second mesh 301 extends for an angle 303 approximately 80-85 degrees about the second filter element 299, with the first mesh 300 extending the remaining 275-280 degrees. The second filter element 299 is oriented within the chimney bore 90 so that the second mesh 301 is in position to receive fluid directly from the vessel 74, for deflecting larger particles attempting to exit the device 150. Further, since the chimney 350 also serves as the liquid inlet, the particle filter 89 acts to prevent debris from entering the chimney 350. A filter retaining clamp 302 tightens atop the second filter element 299 to keep the first and second filter elements 296,299 in place atop the frame 290.

Thus, the particle filter 89 serves to prevent larger particles from being blown out the exhaust aperture 84, and fluid formed by filtered particles runs back into the tank 71. When larger particles become affixed to the particle filter 89, those particles themselves can also serve to form a filter medium.

The particle filter 89 ensures that particles no greater than 5 μm are exhausted from the device 70, and are typically in a range of 0.25-5 μm.

The filter 89 of the present invention is an important element. In a particular embodiment, not intended as limiting, during an average hourly treatment approximately 0.9 to 1.4 gallons of liquid disinfectant solution is filtered back into the tank 71 for regeneration as a result of the filter 89, assisting in ensuring that the output of the device is essentially a "dry mist." Without the filter 89, the conversion of approximately 3.0 gallons an hour of solution creates a fog having significantly more dampness therein. With the filter 89 in place, approximately 1.6-2.1 gallons per hour can be converted, although this is not intended as a limitation.

The device 70 additionally comprises an outer shell 94 that encases the inner tank 71 of FIG. 14. The outer shell 94 comprises a mass blower 95 for generating air flow toward the exhaust aperture 84 for accelerating particles exiting therefrom, and reducing coagulation thereof, spreading the particles out and thereby providing faster introduction of the particles into the space to be treated (FIGS. 16A and 16B). The mass blower 95 has a door 96 that is movable between a closed position (FIG. 16A), wherein the particles exit substantially vertically, and an open position (FIG. 16B) wherein the particles are blown away from the mass blower door. Air flow generated via an inlet thus also creates a vacuum over the leading edge of the exhaust, helping to pull particles out of the chimney bore 90. When a fan for the mass blower 95 is turned on, the air pressure generated thereby opens the diverter door 96.

In yet another embodiment 150, believed at the time of filing to represent a preferred embodiment, a reactor vessel 151 is provided that is substantially rectangular (FIGS. 27, 28, and 30). Supported by two walls 152 of the reactor vessel/cascade tray 151 are a plurality of, here, two, reactor cradles 153 each comprising a bottom support plate 154 affixed to a tensor pinching clip 156 via bolts through outer holes 325. The clip 156 comprises a substantially "U"-shaped element having a side 155 extending upward from an inwardly extending support shelf 323 having holes 324 meeting the bottom support plate's holes 325. The clip 156 further has a top 310 and outer portion 311 outwardly and downwardly extending from each of the sides 155, respectively. It will be understood that the use of such clip portions 156 is not intended as a limitation, and that alternative affixing means could be contemplated, such as hooks, etc.

The clip portions 156 are dimensioned to rest atop the opposed reactor vessel walls 152. The suspension distance of the reactor cradles 153 can also be adjusted, for example, with the use of one or more "shims," such as, but not intended to be limited to, a "U"-shaped spacer 320 positionable between the clip's top 310 and reactor vessel wall 152, an upper spacer 321 positionable between the "U"-shaped spacer 320 and the clip's top 310, and a lower spacer 322 positionable between the bottom support plate 154 and the clip's support shelf 323, and having holes 326 meeting holes 324,325. The adjustability of the reactor cradles 153 is for achieving optimal reaction points with a plurality of liquids having, for example, different specific gravities and different chemical formulations, including different surfactant formulations. The important feature is the ability to control and reproducibly set this suspension distance to achieve optimal conversion rates of liquid volume per time, since the reactor vessel 151 during operation is preferably kept in a "cascading" state, wherein there is no space between the walls' top edges 161 and the fluid level therein. This feature has been found to almost double the conversion rate over previously used structures.

In a preferred embodiment, the reactor cradles 153 and reactor vessel 151 are dimensioned so that their respective walls are closely opposed. Two reactor cradles 153 in this embodiment 150 are adapted for being positioned substantially parallel to each other, although this particular arrangement is not intended to be limiting.

It will be understood by one of skill in the art that the design choices in the reactor vessel 151 and reactor cradles 153 can also include features for adjusting configurations thereof. For example, the reactor cradles 153 can be adjusted in a horizontal plane to accommodate different widths, heights, and configurations of the reactor vessel 151.

Each of the reactor cradles 153 can be affixed atop thereof two "X"-shaped reactor holders, substantially as described above for embodiment 70 (FIG. 13). Reactor heads 43 can then be positioned therein, and retained in place with the use of a clamp 157 and bolt 158 arrangement positioned between the reactors 43. This positioning permits a precise placement of the reactor heads 43 relative to the reactor vessel 151, here, a distance 160 of 1.5 in. from the top edges 161 of the reactor vessel walls 152. The bottom faces 162 of the reactor cradles 153 are positioned in spaced relation from a bottom 163 of the reactor vessel 151, which has been found to enhance the cooling of the solution therein, thereby prolonging the life of the reactors 43 by maintaining them in a cooler state. This arrangement also facilitates repair and/or replacement of the reactors 43 and/or ultrasonic disks 44 as needed, and further permits adjustment of the reaction focal point vertically and horizontally under the air pressure zone of the apparatus 150.

The reactor holders 157 are affixed in staggered relationship on each of the reactor cradles 153, as can be seen in the plan view of FIG. 28, permitting a closer packing of reactor heads 43 within the reactor vessel 151.

This embodiment 150 has been found to maximize microparticle output by stabilizing and optimizing the ultrasonic reaction focal point in or above the solution. Since the reactor heads 43 are secured to the reactor vessel 151, the possibility of misalignment and movement are substantially eliminated.

Figure 30:
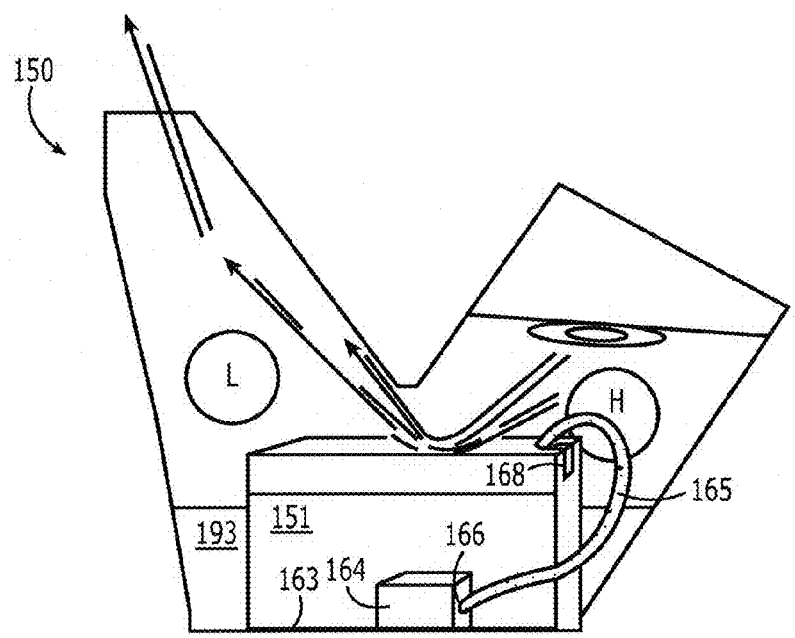
FIG. 30 is a side cutaway view of the device of FIG. 28, illustrating the position of the pump.

Further, in this embodiment 150 a pump 164, comprising a submersible magnetic centrifugal pump in a preferred embodiment, is used to transfer sanitizing liquid to be atomized into the reactor vessel 151 via tubing 165 (FIG. 30). The tubing 165 has a first end 166 in fluid communication with the pump 164 and a second end (not shown) positioned within the reactor vessel 151 adjacent the bottom 163 thereof, and is kept in this position with the use of a clamp 168, for example, a tensor pinching clasp, to affix the tubing 165 to the top edge 161 of the reactor vessel 151. This positioning permits continuous filling and overflowing of the reactor vessel 151 during pump operation, and further permits a siphoning out of liquid when the pump 164 is turned off, and requires no holes to be made in the reactor vessel 151.

Figure 17:
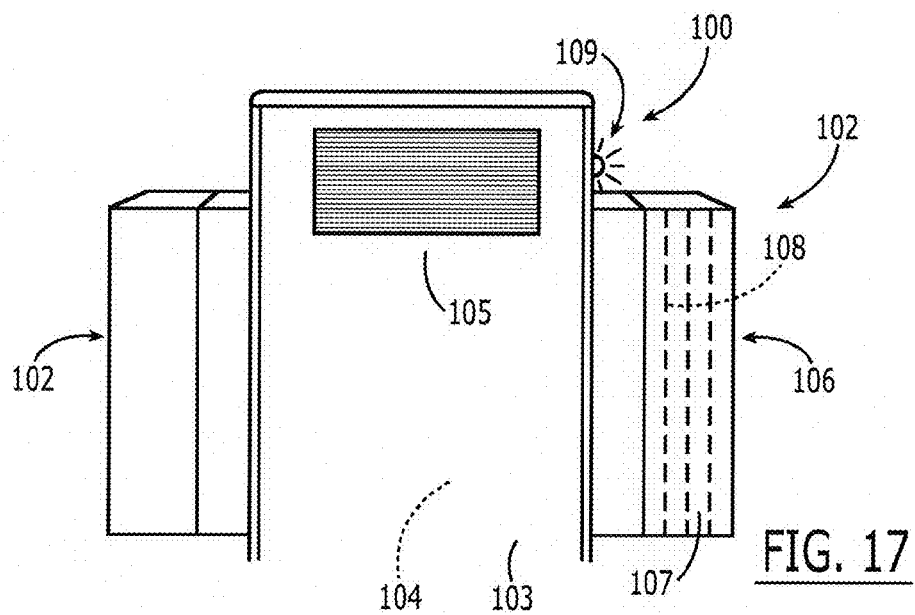
FIG. 17 is a front view of the scrubbing device of the present invention.
Figure 18:
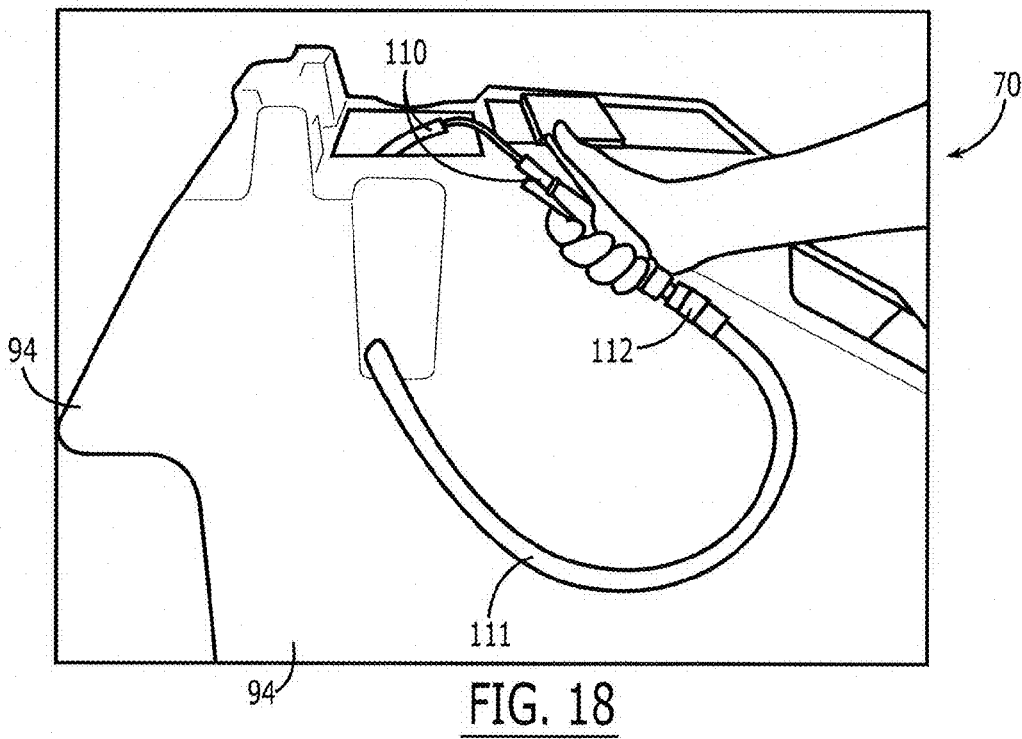
FIG. 18 illustrates the spray nozzle connection.
Figure 19:
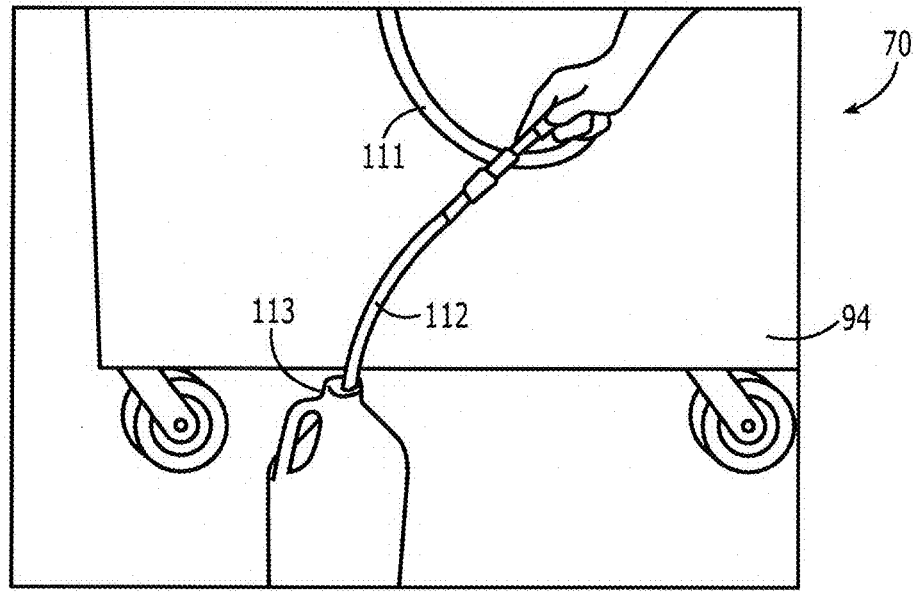
FIG. 19 illustrates the use of a discharge hose to empty the tank of fluid.
Figure 20:
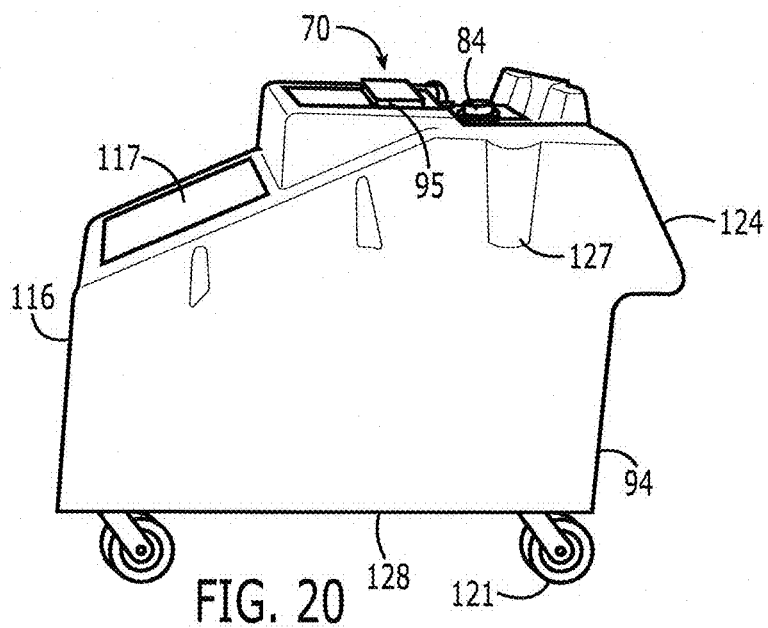
FIG. 20 is a side view of an embodiment of the sanitizing device.
Figure 21:
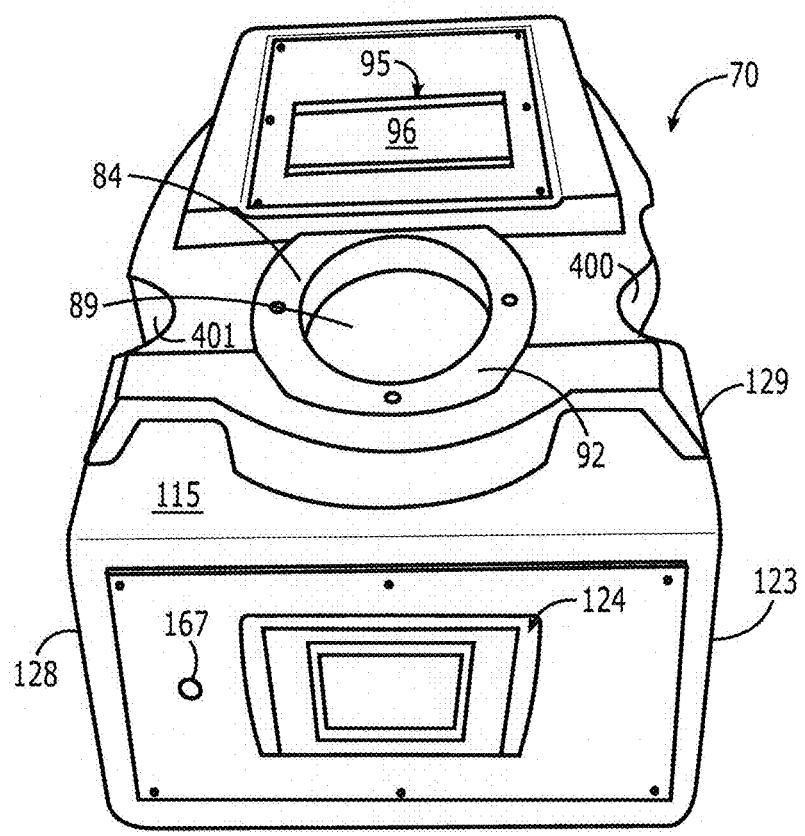
FIG. 21 is a rear view of the device of FIG. 20.
Figure 22:
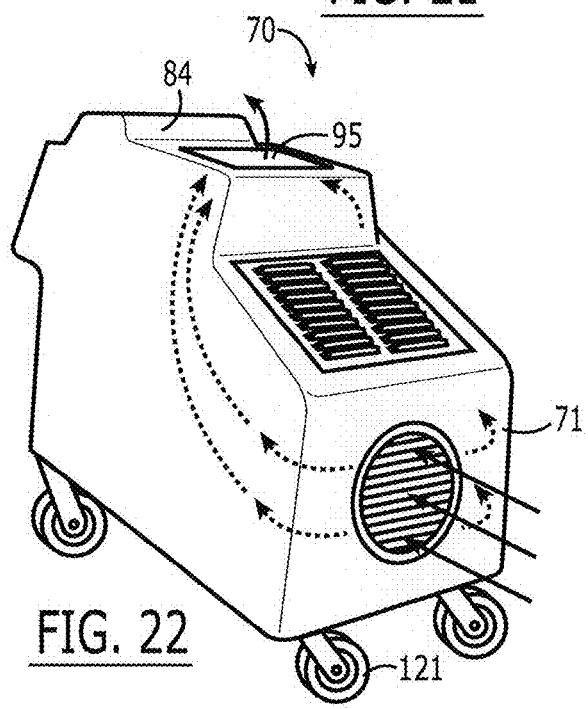
FIG. 22 is a top/front view of the device of FIG. 20.
Figure 23:
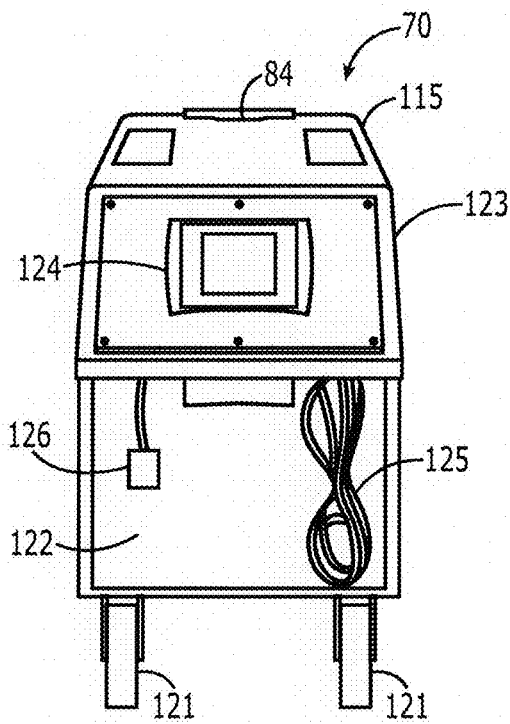
FIG. 23 is a rear view of the device of FIG. 20.
Figure 24:
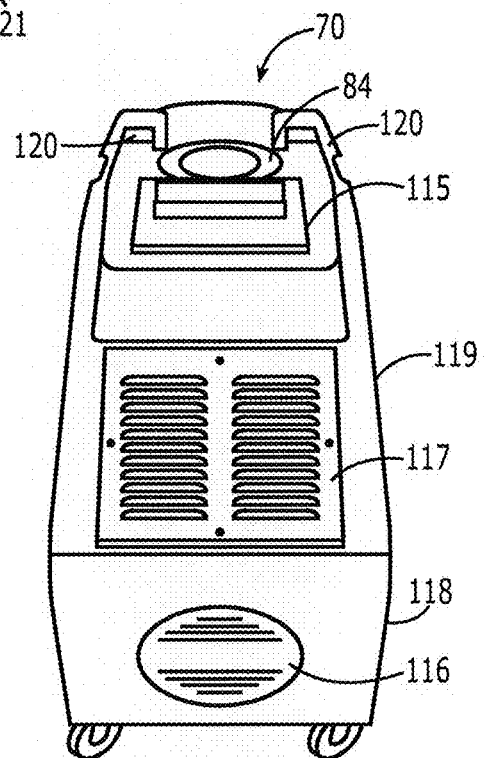
FIG. 24 is a top/front view of the device of FIG. 20.

Yet a further feature of the embodiments 70,150 is a microparticle evacuation device 100 for scrubbing air in the treated space to remove any remaining particles, and also for creating an additional air current within the space to assist particles to attach to surfaces within the space (FIG. 17). This device 100 reduces the time required for reoccupation of the treated space, and is operated for a sufficient time to scrub the air multiple times (e.g., six to eight or more), typically at a rate of 2500-3000 $ft^3$/min. A deodorizer can also be added in the airflow of the scrubber 100 if desired.

The air scrubbing device 100 is connectable to the treatment device 70,150, and uses 120 Vac in a particular embodiment, connected to a source of electricity separately from the treatment device 70,150. The scrubbing device 100 can be operated via, for example, a touch screen positioned on the treatment device 70,150, to which it can be connected via an "umbilical" line insertable into an input 167 (FIG. 21) on the device 70,150 for passing signals therebetween. The scrubbing device 100 can also be operated independently of the treatment device 70, in a "manual" mode. The scrubbing device 100 comprises a pair of series of air filters 102 positioned on a base 103 in opposed relation, each leading to an inner space 104 from which filtered air is expelled through an exhaust 105. Each of the series of air filters 102 can comprise, for example, a ¾-in. metal mesh 106 upstream of a 1¾ HEPA-style filter 107, which in turn is upstream of a 4-in. mini-pleat (95%) filter 108. An indicator light 109 can also be provided that at a predetermined vacuum load, illuminates when the filters 102 need to be changed. A plurality of scrubbers 100 can also be connected in series and operated simultaneously if desired. Other elements may be added as desired, such as, but not intended to be limited to, ultraviolet lights, needle-point ionizers, and/or ozone generators.

The "plumbing" aspect of the device 70 includes additional spray and fluid discharge features. The fluid, for example, can be administered directly (i.e., not in particulate form as generated by the ultrasonic head arrays) by way of a spray attachment 110 connectable to a hose 111 in fluid communication with the inner tank 71 (FIGS. 14, 18, and 21). The spray attachment 110 can be connectable to the hose 111, for example, a quick disconnect, and the hose 111 is retractable within the outer shell 94 adjacent an indentation 400 on one side thereof. The quick disconnect has a safety foot valve that is operator controlled to prevent fluid discharge when disconnected.

Another hose, positioned on an opposite side from the administration hose 111 in another indentation 401 can also be used to drain and empty the tank 71 when the device 70 is not in use (FIG. 19). For this operation, a discharge hose sector 112 is connected to the hose 111, and the sprayer pump is used to discharge fluid for storage into, for example, a bottle 113 or other container.

The entire outer shell 94 and external components of this embodiment 70 are depicted in FIGS. 20-24, although these details are not intended to be limiting. The treatment exhaust 84 and mass blower 95 are positioned on the top 115 of the device 70, with the air inlets 116,117 to the mass blower 95 and the inner tank 71 on the front 118 and slanted upper faces 119, respectively. Handles 120 are provided, as well as wheels 121 for ease of movement. A controller 122 is positioned on the rear 123 of the device 70, along with a touch screen 124, power cord 125, and plug 126. The drain attachment and hose can be on one side 128, and the sprayer hose 111 on the other side 129, although this configuration is not intended as a limitation.

An outline of the inner tank 71 is shown in FIG. 14, along with the air flows to the treatment blower 95 and into the inner tank 71.

Yet a further aspect of the present invention is directed to an element for detecting a level 85 (FIG. 14) of fluid remaining in the tank 71, which has been found to eliminate false readings that can be caused by environmental issues such as coagulation, condensation, and temperature inversions. The sensor apparatus 180 (FIG. 29) in a particular embodiment comprises an enclosed element such as, but not intended to be limited to, a center tube 181. The tube 181 at a bottom end 182 has a bottom opening 183 into which a floatation element 186 is inserted and retained therein with a bottom cap 185 and bottom rubber 184, retained by cap 178. A liquid inlet hole 179, having a diameter, for example, of ¼ in., is positioned on the bottom cap 185 of the sensor apparatus 180, the liquid inlet hole 179 for admitting surrounding liquid, the level of which is desired to be sensed (FIG. 28). At a top end 187 of the center tube 181 is a coupler 188 surmounted by a top cap 189 into which is inserted a PVC ring 190, which supports a sensor holder 191. The sensor holder 191 in turn supports an ultrasonic sensor 192. An air ventilation hole is located adjacent the top end of the sensor apparatus adjacent the top cap 189.

The sensor apparatus 180 is insertable into the tank fluid 193, a fluid level of which reflects that 85 in the tank 71. The flotation element, which may comprise, for example, a plastic disk 186, floats on the fluid 193. The sensor apparatus 180 can be adjusted and oriented as desired. The sensor apparatus 180 can be supported within the tank 71 adjacent the coupler 188 with the use of a plate 340 affixed within the tank 71 having a hole 341 therethrough dimensioned for admitting the coupler 188 (FIG. 28). A substantially inverted-"U"-shaped bracket 342 is affixed to the plate 340 atop the hole 341. The bracket has a hole 343 that is smaller than the plate hole 341, and is dimensioned for admitting the ring 190.

In use, the ultrasonic sensor 192 senses a distance between it and the plastic disk 186 and communicates the sensed data via a signal to a processor, which is in signal communication with a display for indicating the sensed fluid level 85.

Figure 25:
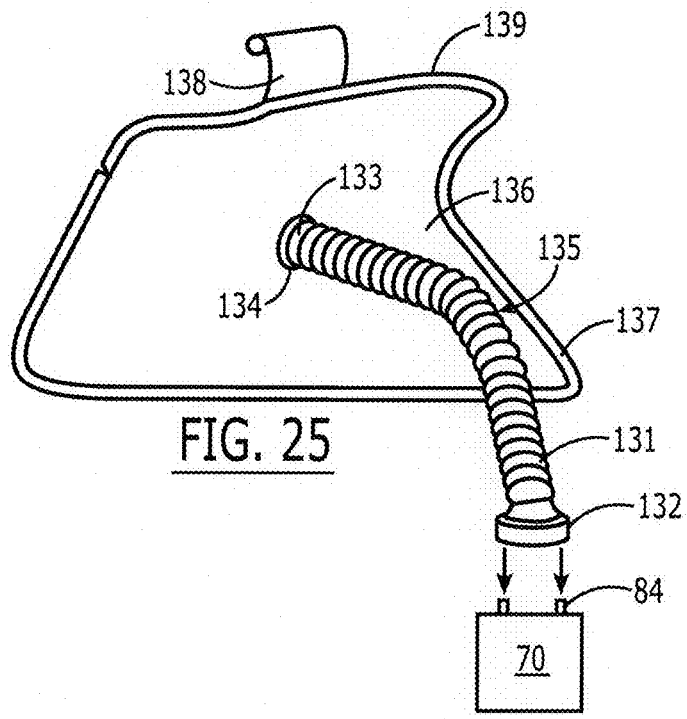
FIG. 25 is a front perspective view of a device for sanitizing a vehicle.
Figure 26:
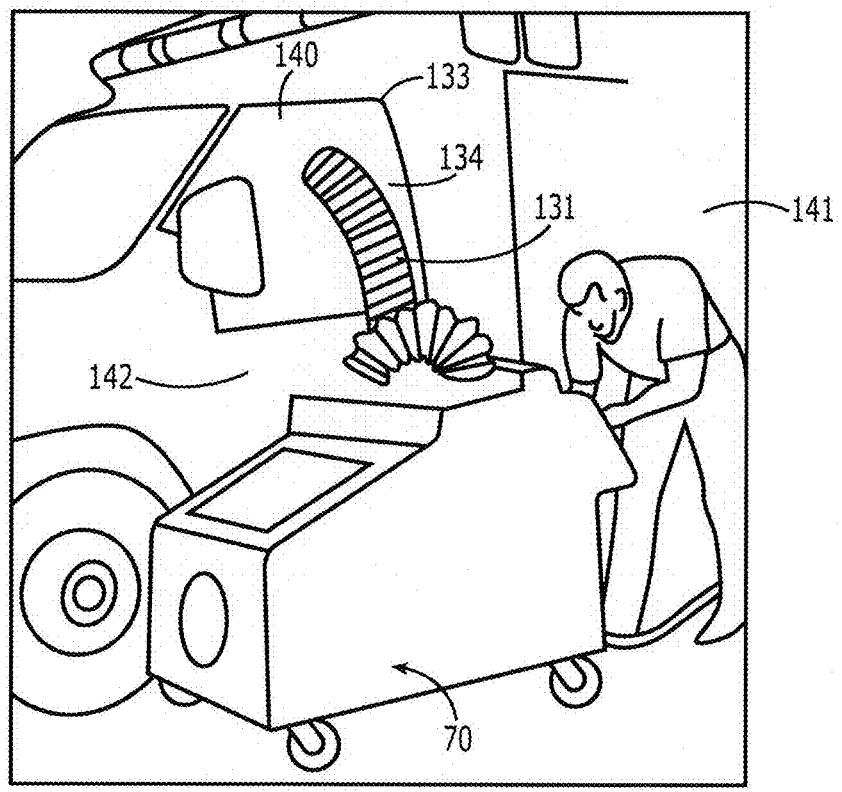
FIG. 26 is a side perspective view of the device of FIG. 25 in use.
Figure 27:
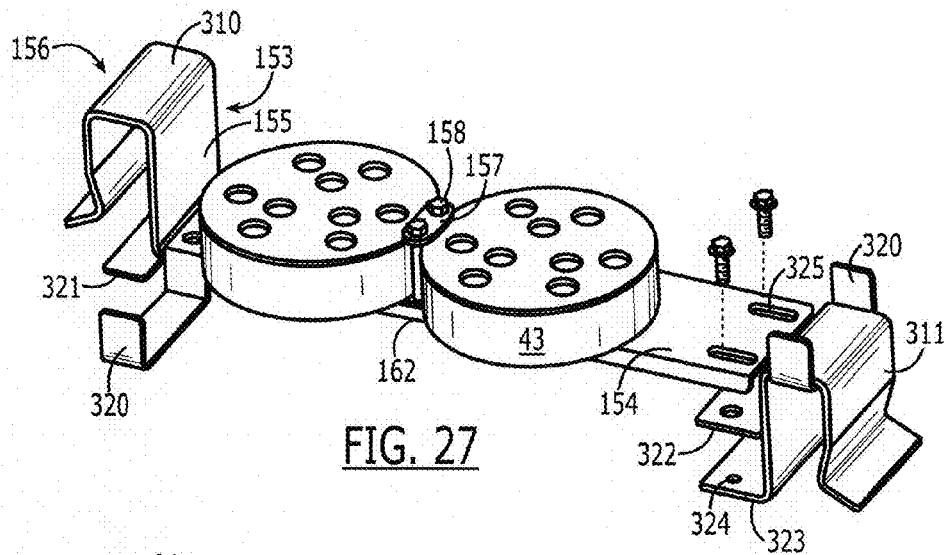
FIG. 27 is a top/side perspective view of an alternate embodiment of a reactor vessel and bracket assembly.

Another aspect of the present invention is directed to a system 130 and method for sanitizing vehicle interiors (FIGS. 25 and 26). The system includes the device 70 as outlined above, and further comprises a hose 131 having a proximal end 132 that is affixable in fluid communication with the exhaust outlet 84. The distal end 133 of the hose 131 is affixable to an aperture 134 in a window seal element 135. In a particular embodiment, the window seal element 135 comprises a flexible, substantially planar overlay 136 having a magnetic seal edge 137 around the perimeter of the overlay 136. In a particular embodiment, the overlay 136 can comprise a vinyl material, although this is not intended as a limitation. Also in a particular embodiment, the hose 131 comprises a serpentine, 6-in.-diameter hose that can extend between 6 and 12 feet to enable its use in virtually any size vehicle. A top retaining tab 138 extends from a top edge 139 of the overlay 136, and the aperture 134 is positioned centrally in the overlay 136. In some embodiments, the system can include one or more hose couplings to enable different hose lengths to be used for different applications, for example, for vehicles, marine vessels, and aircraft.

In use, a window 140 of a vehicle 141 is at least partially rolled down, and the vehicle door 142 is opened. The top retaining tab 138 is placed over the top of the door 142, and the window seal element 135 drapes down over the window 140. The door 142 is closed, and the magnetic seal edge 137 is pressed against the exterior of the door 142.

Next the hose 131 is attached to the fogging unit's exhaust 84, and the unit 70 is activated for a sufficient time to sanitize the vehicle's interior. Other types of interfaces, which could in some cases be permanently installed, could also be contemplated for vehicles or marine vessels so that use of the unit 70 is facilitated.

Another important feature of the present invention includes the liquid composition used for sanitizing spaces, and a method of making this composition. The invention is not intended to be limited, however, to the precise composition and proportion of ingredients in the liquid.

In an embodiment, an additive that can be incorporated into the liquid to be atomized, depending upon the characteristics thereof, can be made as follows: 40 gallons of clean, reverse-osmosis carbon-filtered water is added to a clean plastic or stainless steel vessel, and a mixer is turned on. One pound of sodium metasilicate pentahydrate is mixed into the water slowly, and mixing continues for 5 min. With the mixer still running, a clean plastic vessel is used to remove 1 gal of mixed solution for use in a pre-blending step. 70 ml of SE25 (Wacker Chemie AG, Munich, Germany), a silicone-based, food grade, antifoaming agent, is added to the pail, and mixed using a clean plastic rod until the solution is blended thoroughly. At this point the solution appears to be a cloudy micro-emulsion. 60 ml of K-2 surfactant (Lonza Chemical Corporation, Switzerland), used as a molecular coupler, is mixed slowly into the micro-emulsion until thoroughly blended.

With the mixer running, the pre-blend is added back into the first vessel at a rate of 180 ml per min while the mixer is running, and the mixer continues to run after the pre-blend has been added. Into a clean 1000-ml beaker containing 700 ml reverse osmosis carbon-filtered water, 2 oz of Palaklor-1103041 (Pylam Products Company, Inc., Tempe, Ariz.) is added. This substance comprises a dye base for its ultraviolet reflective traits and can be used as tracer. The Palaklor is not necessary for the dry mist-optimizing aspect of the inventive composition, and can therefore be omitted if a tracer is not desired in the mixture. The mixture is shaken for 1 min, and is then added to the first vessel with continued mixing.

Water is added to the first vessel to bring the volume up to 55 gal, and mixing continues for 15 min. When blending is complete, the mixture stands for 1 h prior to packaging. For use, the mixture is diluted 1:1 with reverse osmosis carbon-filtered water.

To the mixture may be added sanitizing, disinfectant, and/or pesticidal elements such as, but not intended to be limited to, di-N-alkyl($C_{8-10}$)—N,N-dimethylammonium chloride, N-alkyl ($C_{10-12}$)dimethylammonium chloride, tetrasodium ethylenediamine tetraacetate, sodium ethanol, 2-propanol, pyrethrum, octylphenoxypolyethoxyethanol (a nonionic surfactant), quaternary ammonia, formaldehyde, gluteraldehyde, hydrogen peroxide, chlorine dioxide, and electrolyzed brine known as Suprox A and B and ANK (PTA, Ltd., UK). The composition(s) that can be added can be chosen based upon characteristics of the constituents, such as the specific gravity and composition of the sanitizing, disinfecting, sterilizing, and/or pesticidal elements. The compositions of different solutions of the mixture comprising the dry-mist optimizer may be preferable for optimizing the dry mist; such elements may also be converted to dry mist without the mixture.

The composition when added to the disinfectant elements has been shown to kill pathogens of hepatitis B and C, *staphylococcus aureus, streptococcus*, avian influenza, methicillin-resistant *staphlococcus aureus* (MRSA), *enterococcus* bacteria, HIV, *E. coli, pseudomonas, salmonella, listeria*, Legionnaire's disease, human coronavirus, toxic molds, fecal coliform, athlete's foot, and *Clostridium difficile* among others. Further, the composition when added to disinfectant elements enables a reduced surface tension and reduced foaming.

Tests have been conducted with the device and composition of the present invention with disinfectant elements. Most of the particles produced by the device were measured to be in a range of 0.3-0.5 μm. The kill rates achieved with an intermediate-strength quaternary disinfectant are similar to those obtained by other systems known in the art that use highly corrosive oxidizing sterilants, such as hydrogen peroxide gas. It is believed, although not intended as a limitation, that the success is at least in part owing to the size of the particles produced by the system, which is not known to have been achieved heretofore.

In a particular case, for example, a test was conducted on 3.0 billion CFUs of sporing *Clostridium difficile* with a 20-minute treatment and 20-minute dwell time. The treatment resulted in an 80% kill rate, an unexpected result, because the disinfectant used is not supposed to be able to kill this spore, and typically an oxidizing sterilant would be required to kill this spore.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and composition illustrated and described herein are by way of example, and the scope of the invention is not limited to the exact details of construction, constituents, and proportion.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A device for sanitizing and disinfecting a space comprising:
   a tank having an interior space for holding an aqueous sanitizing and disinfecting liquid, the tank having a bottom sector, an air inlet sector having an air inlet therein and an inner wall, and an exhaust sector having an exhaust outlet therein and an inner wall facing the air inlet inner wall, the exhaust sector inner wall and the air inlet sector inner wall forming a substantially V-shaped air pathway within the interior space, the V-shaped air pathway forming a notch generally central therein;
   a reactor vessel positioned within the bottom sector of the tank, a top edge of the reactor vessel in spaced relation to and generally proximate a notch of the V-shaped air pathway;
   an ultrasonic head support comprising means for supporting an ultrasonic head comprising an ultrasonically vibratable disc for generating ultrasonic energy, the ultrasonic head support positionable within and beneath a top edge of the reactor vessel;
   means for transferring liquid from the tank interior space to the reactor vessel to a level for substantially submerging an ultrasonic head supported therewithin, the ultrasonic head vibratable to form atomized micro-particles from the aqueous sanitizing and disinfecting liquid;
   means for drawing air into the air inlet across the reactor vessel and for exhausting the formed atomized micro-particles from the exhaust outlet; and
   a particle filter positioned in an airflow pathway within the exhaust sector;
   wherein the particle filter comprises a plurality of layers, the layers comprising a support frame having apertures of a first size therethrough, a first filter element positioned in surrounding relation to the support frame and having apertures of a second size therethrough, and a second filter element positioned in surrounding relation to the first filter element and having apertures of a third size therethrough, the first size greater than the second size, the second size greater than the third size.

2. The space-sanitizing and -disinfecting device recited in claim 1, wherein the first filter element comprises a 0.25-in. plastic mesh and the second filter element comprises a 0.088-in. plastic mesh covering a first portion of the first filter element and a 0.05-in. plastic mesh covering a second portion of the first filter element distinct from the first portion.

3. The space-sanitizing and -disinfecting device recited in claim 1, wherein the support frame, the first, and the second filter element comprise substantially inverted conical-shaped elements.

4. A device for sanitizing and disinfecting a space comprising:
   a tank having an interior space for holding an aqueous sanitizing and disinfecting liquid, the tank having a bottom sector, an air inlet sector having an air inlet therein and an inner wall, and an exhaust sector having an exhaust outlet therein and an inner wall facing the air inlet inner wall, the exhaust sector inner wall and the air inlet sector inner wall forming a substantially V-shaped air pathway within the interior space, the V-shaped air pathway forming a notch generally central therein;
   a reactor vessel positioned within the bottom sector of the tank, a top edge of the reactor vessel in spaced relation to and generally proximate a notch of the V-shaped air pathway;
   an ultrasonic head support comprising means for supporting an ultrasonic head comprising an ultrasonically vibratable disc for generating ultrasonic energy, the ultrasonic head support positionable within and beneath a top edge of the reactor vessel;
   means for transferring liquid from the tank interior space to the reactor vessel to a level for substantially submerging an ultrasonic head supported therewithin, the ultrasonic head vibratable to form atomized micro-particles from the aqueous sanitizing and disinfecting liquid; and
   means for drawing air into the air inlet across the reactor vessel and for exhausting the formed atomized micro-particles from the exhaust outlet;
   wherein the ultrasonic head support comprises a substantially U-shaped reactor cradle supported by the reactor vessel top edge, the reactor cradle comprising means for supporting a plurality of ultrasonic head arrays, each comprising a plurality of vibratable disks affixed to a top surface of the respective ultrasonic head array.

5. The space-sanitizing and -disinfecting device recited in claim 4, wherein the reactor cradle comprises a pair of reactor cradles, each comprising means for supporting two ultrasonic head arrays and positionable in side-by-side relation to each other.

6. The space-sanitizing and -disinfecting device recited in claim 4, wherein the reactor cradle is adjustably supported by the reactor vessel top edge, for achieving an optimal reaction point relative to the liquid, the liquid-transferring means operable to retain a liquid level in the reactor vessel at a predetermined, substantially constant level.

7. The space-sanitizing and -disinfecting device recited in claim 4, further comprising a sensing device for detecting a level of liquid in the tank.

8. The space-sanitizing and -disinfecting device recited in claim 7, wherein the sensing device comprises a tube positioned within the tank interior space having a hole adjacent a bottom end, a flotation element movably positioned within the tube, an air ventilation hole at a top end, and an ultrasonic sensor adjacent the top end, the ultrasonic sensor adapted to measure a distance from the flotation element, wherein in use liquid enters the tube through the tube hole, floats the flotation element to a level representative of the liquid level in the tank, and the ultrasonic sensor creates a signal based upon the sensed distance from the flotation element.

9. The space-sanitizing and -disinfecting device recited in claim 7, wherein the sensing device is positioned within the tank air inlet sector.

10. A device for sanitizing and disinfecting a space, the device comprising:
- a tank having an interior space, the tank having a bottom sector, an exhaust sector having an inner wall, and an air inlet sector having an inner wall facing the exhaust sector inner wall, wherein the air inlet sector inner wall and the exhaust sector inner wall form a compression region for an air pathway within the interior space, the tank further having an air inlet in the air inlet sector and an exhaust outlet in the exhaust sector;
- an aqueous liquid having at least one of sanitizing, disinfecting, and sterilizing properties carried within the tank interior space;
- a reactor vessel positioned within the tank bottom sector;
- means for continuously transferring the aqueous liquid into the reactor vessel;
- an ultrasonically vibratable disc having an ultrasonic head array to generate ultrasonic energy, the ultrasonic head array positioned within and beneath a top edge of the reactor vessel and submerged within the transferred liquid at a substantially constant emersion depth, wherein the continuously transferring of the liquid and vibratable disk in operation form a plurality of atomized micro-particles therefrom;
- air flow means operable for providing a preselected flow of air within the interior space from the inlet toward the outlet, the air flowing through the compression region from a high pressure to a low pressure, so as to cause smaller particles within the plurality of micro-particles to move more quickly than larger particles thereof, the preselected flow of air allowing at least a portion of the larger micro-particles to fall back to the tank bottom sector and the plurality of micro-particles preferentially enriched with the smaller micro-particles;

a mesh filter having a first cross sectional portion positioned for initially receiving the preferentially enriched micro-particles and a second cross sectional portion downstream therefrom, wherein the first cross sectional portion is smaller than the second cross sectional portion, the mesh filter positioned for passing the preferentially enriched micro-particles through the mesh filter prior to exiting the exhaust outlet for a filtering thereof, and wherein the air flow means results in exhausting the preferentially enriched micro-particles from the reactor vessel through the exhaust outlet to a space exterior of the tank.

11. The device recited in claim 10, wherein the filter comprises a particle filter having a plurality of layers, each layer having a support frame including apertures of a first size therein, a first filter element positioned in surrounding relation to the support frame and having apertures of a second size therein, and a second filter element positioned in surrounding relation to the first filter element and having apertures of a third size therein, wherein the first size aperture is greater than the second size aperture and the second size is greater than the third size aperture.

12. The device recited in claim 11, wherein the first filter element comprises a 0.25-in. plastic mesh and the second filter element comprises a 0.88-in. plastic mesh covering a first portion of the first filter element and a 0.05-in. plastic mesh covering a second portion of the first filter element distinct from the first portion.

13. The device recited in claim 12, wherein the support frame, the first, and the second filter element comprise substantially inverted conical-shaped elements.

14. A device for sanitizing and disinfecting a space comprising:

a tank dimensioned for carrying an aqueous sanitizing liquid in an interior space of a tank, the tank having a bottom sector, an exhaust sector having an inner wall, and an air inlet sector having an inner wall facing the exhaust sector inner wall, the air inlet sector inner wall and the exhaust sector inner wall forming a compression region for an air pathway within the interior space, and further having an air inlet in the air inlet sector and an exhaust outlet in the exhaust sector;

a reactor vessel carried within the tank interior space above a lowermost portion of the bottom sector, the reactor vessel having a cradle;

means for continuously transferring the aqueous sanitizing liquid from the tank interior space to the reactor vessel;

an ultrasonic head array having an ultrasonically vibratable disc, the ultrasonic head array supported by the cradle, wherein each ultrasonic head array comprises a plurality of vibratable disks affixed to a top surface of the ultrasonic head array, the ultrasonic head array positioned within and beneath a top edge of the reactor vessel and submerged within the transferred liquid, the ultrasonic head array thus positioned at a substantially constant emersion depth resulting from the continuously transferring liquid step so as to form a plurality of atomized micro-particles during operation thereof;

means for providing a preselected flow of air within the interior space from the inlet toward the outlet, the air flowing through the compression region from a high pressure to a low pressure, so as to cause smaller particles within the plurality of micro-particles to move more quickly than larger particles thereof, the preselected flow of air allowing at least a portion of the larger micro-particles to fall back to the tank bottom sector and the plurality of micro-particles preferentially enriched with the smaller micro-particles; and means for exhausting the preferentially enriched micro-particles from the reactor vessel through an exhaust outlet to a space exterior of the tank.

15. The device recited in claim 14, wherein the reactor cradle comprises a pair of reactor cradles, each comprising means for supporting two head arrays and positionable in side-by-side relation to each other.

16. The device recited in claim 14, further means for detecting a level of the sanitizing liquid in the tank.

17. The device recited in claim 16, wherein the detecting means comprises a tube positioned within the tank interior space, a flotation element movably positioned within the tube for permitting liquid to enter the tube, a flotation element for floating to a level representative of the liquid level in the tank, and signaling means for providing a signal responsive to the liquid level.

18. A device for sanitizing and disinfecting an environment comprising:

a housing having an inlet and an outlet positioned for air flow therebetween;

a reactor vessel carried within the housing;

an aqueous liquid having at least one of sanitizing, disinfecting, and sterilizing properties carried in an interior space of the housing;

air flow means providing an air flow from the inlet to the outlet of the housing;

means for continuously transferring the aqueous liquid from the housing interior space into the reactor vessel;

an ultrasonic head positioned at a preselected and fixed level below a surface of the aqueous liquid in the reactor vessel for forming a plurality of atomized particles to be emitted therefrom;

means for compressing the air flow between the inlet and the outlet for causing air to flow from a high pressure to a low pressure, thus causing smaller particles within the plurality of atomized particles to move more quickly than larger particles therein, the air flow compressing allowing at least a portion of the larger particles to fall away from the outlet and thus preferentially enrich the plurality of atomized particles with the smaller atomized particles; and a mesh filter having a first cross sectional portion positioned for initially receiving the preferentially enriched micro-particles and a second cross sectional portion downstream therefrom, wherein the first cross sectional portion is smaller than the second cross sectional portion, wherein the mesh filter is positioned for filtering the preferentially enriched atomized particles when the particles pass therethrough toward the outlet; and means for exhausting the preferentially enriched atomized particles from the housing into a space outside the housing.

19. The device recited in claim 18, wherein particles having a first size and particles having a second size exit the mesh filter, and wherein the exhausting means is operable for exhausting only the first sized particles into the outside space, and allowing the second sized particles to be deposited into the aqueous liquid.

20. The device recited in claim 19, wherein the exhausted atomized particles are sized to not exceed five microns.

21. The device recited in claim 18, wherein the mesh filter comprises a conical shape having an apex and a base thereof, and wherein the apex is upstream the base within the air flow.

* * * * *